US00PP18354P2

(12) United States Plant Patent
Oudshoorn

(10) Patent No.: US PP18,354 P2
(45) Date of Patent: Dec. 25, 2007

(54) ***EUPATORIUM* PLANT NAMED 'PHANTOM'**

(50) Latin Name: *Eupatorium hybrida*
Varietal Denomination: Phantom

(75) Inventor: Hubertus Gerardus Oudshoorn, AB Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/494,116

(22) Filed: Jul. 27, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
(74) *Attorney, Agent, or Firm*—C. A. Whealy

(57) ABSTRACT

A new and distinct cultivar of *Eupatorium* plant named 'Phantom', characterized by its compact and upright plant habit; basal branching habit; freely flowering habit; and inflorescences with red purple-colored disc florets.

1 Drawing Sheet

Botanical designation: *Eupatorium hybrida.*
Cultivar denomination: 'Phantom'.

BACKGROUND OF THE INVENTION

The present invention relates to a new and distinct cultivar of *Eupatorium* plant, botanically known as *Eupatorium hybrida,* and hereinafter referred to by the name 'Phantom'.

The new *Eupatorium* is a product of a planned breeding program conducted by the Inventor in Rijpwetering, The Netherlands. The objective of the breeding program is to create new compact *Eupatorium* cultivars with attractive flower coloration.

The new *Eupatorium* originated from a cross-pollination by the Inventor in 2002 of an unnamed selection of (*Eupatorium maculatum* cultivar Atropurpureum× *Eupatorium rugosum*)×*Eupatorium maculatum* cultivar Atropurpureum, not patented, as the female, or seed, parent with the *Eupatorium maculatum* cultivar Atropurpureum, not patented, as the male, or pollen, parent. The new *Eupatorium* was discovered and selected by the Inventor as a single flowering plant from within the progeny of the stated cross-pollination grown in a controlled environment in Rijpwetering, The Netherlands in 2003.

Asexual reproduction of the new *Eupatorium* by softwood cuttings in a controlled environment in Rijpwetering, The Netherlands since 2003, has shown that the unique features of this new *Eupatorium* are stable and reproduced true to type in successive generations.

SUMMARY OF THE INVENTION

The cultivar Phantom has not been observed under all possible environmental conditions. The phenotype may vary somewhat with variations in environment such as temperature and light intensity, without, however, any variance in genotype.

The following traits have been repeatedly observed and are determined to be the unique characteristics of 'Phantom'. These characteristics in combination distinguish 'Phantom' as a new and distinct cultivar of *Eupatorium:*

1. Compact and upright plant habit.
2. Basal branching habit.

3. Freely flowering habit.
4. Inflorescences with red purple-colored disc florets.

Compared to plants of the parents, plants of the new *Eupatorium* are much more compact.

Plants of the new *Eupatorium* can be compared to plants of other selections of *Eupatorium maculatum* and *Eupatorium rugosum* known to the Inventor. Compared to other selections of *Eupartorium maculatum* and *Eupatorium rugosum* known to the Inventor, plants of the new *Eupatorium* are much more compact.

BRIEF DESCRIPTION OF THE PHOTOGRAPH

The accompanying photograph illustrates the overall appearance of the new *Eupatorium.* The photograph shows the colors as true as it is reasonably possible to obtain in colored reproductions of this type. Colors in the photograph may differ slightly from the color values cited in the detailed botanical description which accurately describe the colors of the new *Eupatorium.* The photograph comprises a side perspective view of typical flowering plants of 'Phantom' grown in an outdoor nursery.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Rijpwetering, The Netherlands during the summer and early autumn in an outdoor nursery and under conditions and practices which approximate those generally used in commercial *Eupatorium* production. During the production of the plants, day temperatures ranged from 14° C. to 32° C. and night temperatures ranged from 4° C. to 15° C. Measurements and numerical values represent averages for typical flowering plants. Plants were about one year old when the photographs and description were taken.

Botanical classification: *Eupatorium hybrida* cultivar Phantom.

Parentage:

*Female parent.*—Unnamed selection of (*Eupatorium maculatum* cultivar Atropurpureum×*Eupatorium rugosum*)×*Eupatorium maculatum* cultivar Atropurpureum, not patented.

*Male parent.*—*Eupatorium maculatum* cultivar Atropurpureum, not patented.

Propagation:

*Type.*—By cuttings.

*Time to develop roots.*—About 20 to 30 days at 20° C.

*Time to produce a rooted young plant.*—About 60 to 70 days at 20° C.

*Root description.*—Fine; light brown in color.

*Rooting habit.*—Freely branching; moderately dense.

Plant description:

*Plant form/growth habit.*—Compact and upright plant habit; narrow inverted triangle; basal branching habit; inflorescences held above and beyond the foliage on strong peduncles. Moderately vigorous growth habit.

*Plant height.*—About 94 cm.

*Plant diameter or spread.*—About 55 cm.

*Lateral branches.*—Length: About 65 cm. Diameter: About 7 mm. Internode length: About 10.7 cm. Aspect: Mostly upright to slightly outwardly spreading. Strength: Strong. Texture: Smooth, glabrous. Color: N186C.

Foliage description:

*Arrangement.*—In whorls of three, simple.

*Length.*—About 16.1 cm.

*Width.*—About 6.6 cm.

*Shape.*—Lanceolate to ovate.

*Apex.*—Long apiculate to narrowly acuminate.

*Base.*—Attenuate.

*Margin.*—Serrate.

*Texture, upper surface.*—Smooth, glabrous.

*Texture, lower surface.*—Mostly smooth, pubescence along main veins.

*Venation pattern.*—Pinnate.

*Color.*—Developing foliage, upper surface: 137C. Developing foliage, lower surface: 138A. Fully expanded foliage, upper surface: 139A to 147A; venation, 139A to 147A. Fully expanded foliage, lower surface: 137B; venation, 146C.

*Petiole length.*—About 1 cm.

*Petiole diameter.*—About 4 mm.

*Petiole color, upper surface.*—166A.

*Petiole color, lower surface.*—146C tinged with 166A to 166B.

Inflorescence description:

*Appearance.*—Inflorescences arranged in terminal and axillary compound corymbs. Inflorescences positioned upright above and beyond the foliage on sturdy peduncles. Freely flowering habit; about 1,150 inflorescences develop per plant. Inflorescences persistent.

*Fragrance.*—Slightly fragrant; sweet.

*Time to flower.*—Under natural season conditions, plants flower from late August to late September in The Netherlands.

*Post-production longevity.*—Inflorescences maintain good substance for about three weeks on the plant.

*Inflorescence bud.*—Height: About 7 mm. Diameter: About 2 mm. Shape: Narrowly oblong. Color: 76B to 76C.

*Corymb diameter.*—About 27.5 cm.

*Corymb height.*—About 29 cm.

*Inflorescence size.*—Diameter: About 7 mm. Depth (height): About 1.2 mm. Receptacle diameter: About 3 mm. Receptacle height: About 9 mm.

*Ray florets.*—No ray florets observed.

*Disc florets.*—Shape: Tubular; apex dentate. Length: About 1.2 cm. Diameter, apex: About 2.5 mm. Diameter, base: About 0.5 mm. Number of disc florets per inflorescence: About eleven. Color: Immature: 61A. Mature: Apex: N74C to N74D. Mid-section: N74D to 75B. Base: 75B to 75D.

*Phyllaries.*—Quantity per inflorescence: About 19. Length: About 3 mm. Width: About 1.5 mm. Shape: Narrowly elliptic. Apex: Broadly acute. Base: Cuneate. Margin: Entire. Texture, upper and lower surfaces: Smooth, glabrous. Color, upper and lower surfaces: 75D; towards the base, 145C to 145D.

*Peduncles.*—Length: About 20.4 cm. Diameter: About 2 cm. Strength: Strong. Aspect: Mostly upright to about 20° from vertical. Texture: Smooth, glabrous. Color: N186C.

*Reproductive organs.*—Androecium: Quantity per floret: Five. Anther shape: Linear. Anther length: About 2 mm. Anther color: 187A. Pollen amount: Scarce. Pollen color: Yellow. Gynoecium. Quantity per floret: One. Pistil length: About 8 mm. Stigma shape: Tapering. Stigma color: 76B. Style length: About 5 mm. Style color: 76A. Ovary color: 145A.

*Seeds.*—Length: About 3.5 mm. Diameter: About 0.5 mm. Color: 197A to 197B.

Disease/pest resistance: Plants of the new *Eupatorium* have not been shown to be resistant to pathogens and pests common to *Eupatorium*.

Garden performance: Plants of the new Clematis have exhibited good tolerance to rain and wind and have been observed to be suitable for USDA Zones 6 to 9.

It is claimed:

1. A new and distinct *Eupatorium* plant named 'Phantom' as illustrated and described.

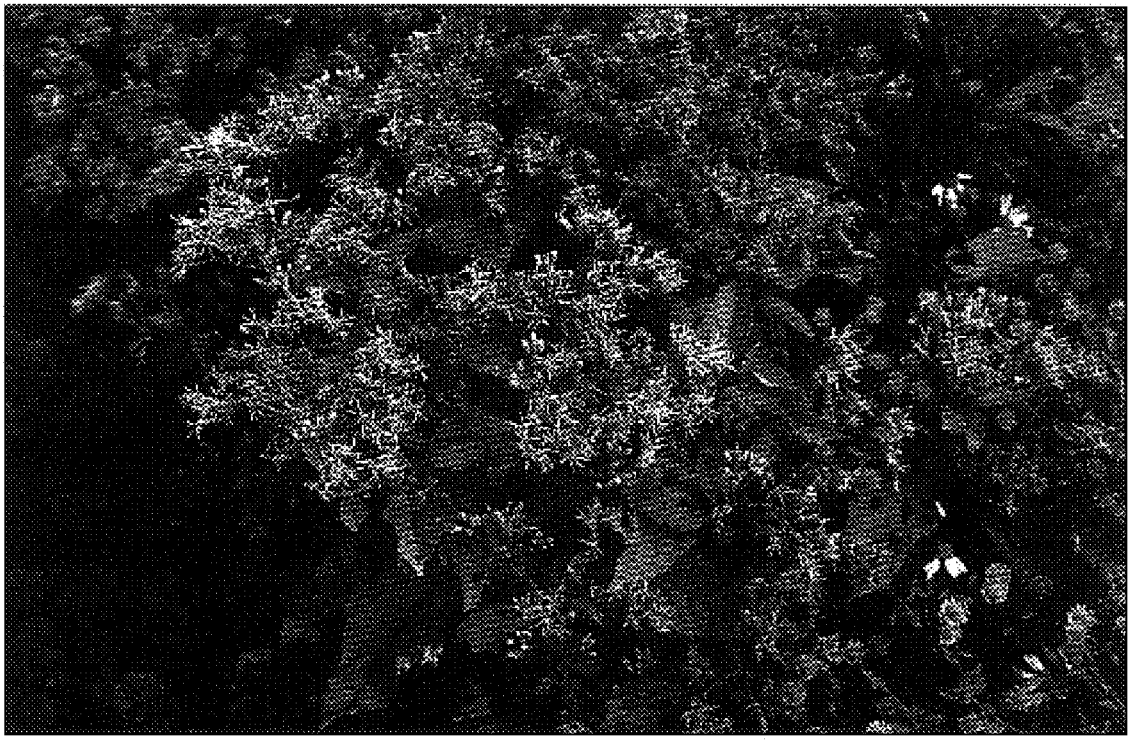

* * * * *